United States Patent
Rudd et al.

[11] Patent Number: 5,645,565
[45] Date of Patent: Jul. 8, 1997

[54] SURGICAL PLUG

[75] Inventors: Ray G. Rudd, Peachtree, Ga.; Douglas E. Sedgwick, New Richmond; Sandra L. Schlosser, Cincinnati, both of Ohio

[73] Assignee: Ethicon Endo-Surgery, Inc., Cincinnati, Ohio

[21] Appl. No.: 489,857

[22] Filed: Jun. 13, 1995

[51] Int. Cl.$^6$ ....................................... A61B 17/00
[52] U.S. Cl. .................. 606/213; 606/1; 128/887; 600/32
[58] Field of Search ................ 606/213, 65, 72, 606/73; 604/285, 174, 175; 128/887; 600/32; 623/11

[56] References Cited

U.S. PATENT DOCUMENTS

| | | | |
|---|---|---|---|
| 57,382 | 8/1866 | Rogers | 222/552 |
| 520,840 | 6/1894 | Banker | 222/552 |
| 1,761,164 | 6/1930 | Wilson | 222/552 |
| 4,852,568 | 8/1989 | Kensey | . |
| 4,890,612 | 1/1990 | Kensey | 606/213 |
| 4,895,148 | 1/1990 | Bays et al. | 606/213 |
| 5,009,643 | 4/1991 | Reich et al. | 604/165 |
| 5,021,059 | 6/1991 | Kensey et al. | 606/213 |
| 5,032,125 | 7/1991 | Durham et al. | 606/73 |
| 5,061,274 | 10/1991 | Kensey | 606/213 |
| 5,127,909 | 7/1992 | Shichman | 604/165 |
| 5,141,515 | 8/1992 | Eberbach | 606/151 |
| 5,192,302 | 3/1993 | Kensey et al. | 606/213 |
| 5,209,736 | 5/1993 | Stephens et al. | 604/164 |
| 5,217,441 | 6/1993 | Shichman | 604/283 |
| 5,254,105 | 10/1993 | Haaga | 604/265 |
| 5,287,852 | 2/1994 | Arkinstall | 128/207 |
| 5,330,445 | 7/1994 | Haaga | 128/642 |
| 5,332,398 | 7/1994 | Miller et al. | 604/175 |
| 5,372,588 | 12/1994 | Farley et al. | 604/164 |
| 5,380,288 | 1/1995 | Hart et al. | 604/167 |
| 5,425,757 | 6/1995 | Tiefenbrun et al. | 606/194 |
| 5,437,649 | 8/1995 | Letchworth | 600/32 |
| 5,443,482 | 8/1995 | Stone et al. | 606/73 |

FOREIGN PATENT DOCUMENTS

| | | |
|---|---|---|
| 0336903 | 4/1989 | European Pat. Off. . |
| WO93/04717 | 3/1993 | European Pat. Off. . |
| 0542432A1 | 5/1993 | European Pat. Off. . |
| WO94/07552 | 9/1993 | European Pat. Off. . |
| 35311 | 6/1908 | Germany ............ 222/552 |

*Primary Examiner*—Jeffrey A. Schmidt
*Attorney, Agent, or Firm*—Matthew S. Goodwin

[57] ABSTRACT

A surgical plug and method are disclosed for minimizing leakage of insufflation fluid from an inflated body cavity through a puncture opening during an endoscopic surgical procedure. The surgical plug and method can be used to maintain insufflation during an endoscopic surgical procedure. The surgical plug includes a cap to plug the puncture opening and seal it, and a shaft extending from the cap into the body cavity. The shaft has helical thread, and the shaft is screwed into and through the opening until the cap is adjacent the body wall through which the opening is made. The surgical plug is stable and can maintain its sealing effect throughout an entire endoscopic surgical procedure. It also does not obstruct or interfere with the field of vision at the surgical site within the body cavity during the procedure. The method of using the surgical plug is simple and straightforward.

12 Claims, 4 Drawing Sheets

SURGICAL PLUG

BACKGROUND OF THE INVENTION

This invention relates to a surgical plug and a method of plugging a puncture wound with a surgical plug during surgery. More particularly, it relates to a plug adapted for minimizing leakage of insufflation fluids within an internal bodily cavity during an endoscopic procedure, and the method of using a surgical plug to prevent leakage during these procedures.

During an endoscopic surgical procedure, a pressurizing fluid such as carbon dioxide gas is pumped into the body cavity to separate organs from one another so that the surgeon has room to maneuver surgical instruments within the surgical site during the procedure. When the body cavity is pumped with the inflation fluid, the "insufflated" body cavity must be maintained in this condition during the procedure. Therefore, puncture wounds made to provide a passageway into the body cavity must be sealed against leakage of the insufflation fluid from the body cavity through the puncture. Additionally, surgical instruments inserted through the puncture into the body cavity must also be sealed to prevent leakage of the insufflation fluid from the body cavity through the instrument. Therefore, the instruments which provide a passageway into the body cavity and instruments which can manipulate body tissue to perform an operative procedure have sealing mechanisms to prevent leakage and therefore maintain the body cavity in the insufflated state. These instruments include trocar assemblies which incorporate a flapper valve within a tubular passageway referred to as a trocar "cannula", and endoscopic clip appliers and staplers, which have different sealing mechanisms to obstruct the flow of insufflation fluid through the instrument.

Although endoscopic surgical instruments incorporate seals to maintain insufflation, it sometimes becomes necessary to remove these instruments during surgery and expose an open puncture wound where insufflation fluids can freely escape from the body cavity. For example, a surgeon may inadvertently place a trocar cannula in the wrong position. Although the trocar cannula seals the puncture wound, the surgeon may want to remove the inadvertently placed trocar cannula and reposition the cannula at another location. When the cannula is removed, the puncture wound with the opening it defines will not be sealed. Additionally, it may be desirable to carry out certain procedures without using trocar cannulas to seal the passageway into the body while various instruments are inserted and withdrawn. In these instances, when an instrument is withdrawn from the body cavity, the puncture opening is exposed and insufflation fluids can leak from the body cavity through the opening.

It is therefore desirable to provide a simple sealing device to maintain insufflation during an endoscopic procedure which can easily and effectively seal a puncture opening which has provided access to a surgical site within a patient's bodily cavity. It would also be desirable if a surgical method were developed to maintain an insufflated body cavity during a surgical procedure when a puncture opening providing access to the surgical site within the body cavity needs to be sealed in a straightforward and effective manner to maintain the insufflation. Furthermore, it would be beneficial if such a surgical sealing device and method could be developed which can provide these objectives without sacrificing the field of vision at the surgical site during the endoscopic surgical procedure. Finally, it would be especially desirable if such a device and surgical method could accomplish all of these objectives and yet also provide a device which is stable so that the surgeon can be assured of an effective seal during the entire procedure.

SUMMARY OF THE INVENTION

In one aspect, the invention is a surgical plug for minimizing leakage of insufflation fluid during an endoscopic surgical procedure. The plug minimizes leakage from within an interior body cavity of a surgical patient through an opening of a given diameter made in the body wall of the patient to provide access to the body cavity. The plug comprises an impervious cap having a diameter greater than the opening diameter. The cap is disposed exteriorly of the body cavity and adjacent the body wall for plugging the opening. A generally cylindrical shaft extends from the cap. The shaft extends interiorly into the interior body cavity of the patient. The shaft has an outer surface and proximal and distal ends. The outer surface has a helical thread on it from adjacent the proximal end to adjacent the distal end. The thread facilitates the insertion of the shaft through the opening into the interior body cavity.

In another aspect, the invention is a surgical method of plugging a puncture opening of a given diameter in a body wall of a patient. The method is used to minimize leakage from within an inflated internal bodily cavity through the opening during an endoscopic surgical procedure. The method initially comprises the step of providing a surgical plug having an impervious cap with a cap diameter greater than the opening diameter. A generally cylindrical shaft extends from the cap. The shaft has a shaft diameter greater than the opening diameter, an outer surface and proximal and distal ends, a helical thread on the outer surface which extends from adjacent the shaft proximal end to the shaft distal end, and a point at the shaft distal end. When the surgical plug having the characteristics set forth above is provided, the surgical method further comprises the steps of inserting the point on the shaft distal end of the plug into and through the opening, and then screwing the shaft through the opening until the distal end of the shaft descends internally into the body cavity and the cap is adjacent to the opening.

The surgical plug of this invention easily and effectively provides an adequate seal at a puncture opening to maintain insulation during an endoscopic surgical procedure. Likewise, the surgical method of this invention provides a straightforward method for a surgeon to plug the puncture opening to minimize leakage from an inflated body cavity through the opening during an endoscopic surgical procedure. The helical thread extending from the proximal to the distal ends of the shaft of the surgical plug facilitates insertion of the plug into the body cavity to seal the opening. In addition, the surgical plug provides adequate stability when the plug is inserted to seal the opening, and consequently it provides desired stability throughout the entire surgical procedure. Furthermore, it provides this desired stability and ease of use without interfering with the field of vision at the surgical site within the body cavity.

The surgical plug and method of plugging a puncture opening of this invention can be used during any endoscopic surgical procedure where it is desirable to seal a puncture opening providing access to a body cavity to maintain insufflation.

BRIEF DESCRIPTION OF THE DRAWINGS

A most preferred embodiment of this invention is described below in connection with the illustrations depicted in the drawings. The drawings can briefly be described as follows.

BRIEF DESCRIPTION OF THE PREFERRED EMBODIMENTS

Figure 1:
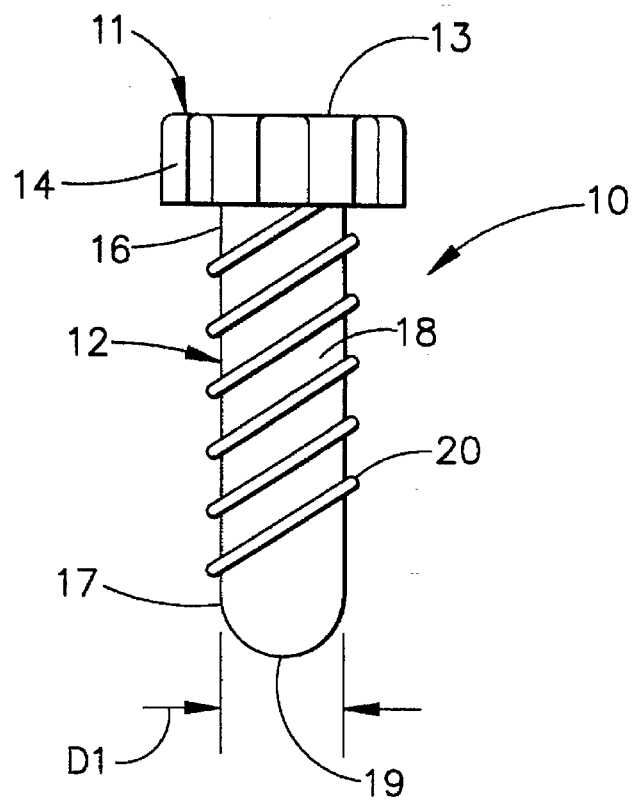
FIG. 1 is a side elevation view of a surgical plug within the scope of the claimed invention.
Figure 1A:
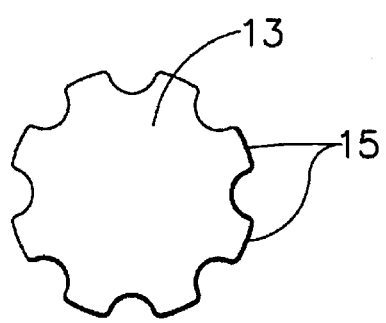
FIG. 1a is a top plan view of the plug of FIG. 1.

Referring to FIGS. 1 and 1a, there is shown a surgical plug 10 of this invention. Overall, it has the general characteristics of a blunt-tipped screw with a blunt tip. The plug has two basic components. These components are a cap 11 and a shaft 12.

The cap is an impervious cap which provides a convenient gripping surface for insertion of the plug and adequately covers the opening made in the body wall to confidently minimize or prevent insufflation fluids from leaking from the body cavity. The cap has a generally circular, flat top surface 13 and a continuous sidewall surface 14 descending integrally from the top flat surface. The circumference of the sidewall surface is substantially identically to that of the top flat surface. The side,will surface displays a plurality of knurled ridges 15 evenly spaced along the periphery of the surface. The ridges provide a gripping surface to more efficiently manipulate the plug. The diameter of the cap is sized greater than the diameter of the opening in the body wall so that when the plug is inserted through the body wall, the cap covers the opening.

The shaft 12 is a cylindrical shaft which has proximal and distal ends 16 and 17, respectively, and an outer surface 18. The proximal end of the shaft is attached to the underside of the top flat surface of the cap. The distal end of the shaft terminates at a point which is a blunt tip 19. The blunt tip of the shaft helps to minimize trauma when the plug is inserted through the body wall. A helical thread 20 is displayed on the outer surface of shaft from the proximal to the distal end of the shaft. The length of the shaft should be sized such that when the plug is inserted through the body wall so that the cap is adjacent the body wall, the shaft is long enough to descend through the body wall into the interior of the body cavity. The diameter of the shaft, designated as "D1" on FIG. 1, is desirably greater than the diameter of the opening in the body wall.

Figure 2:
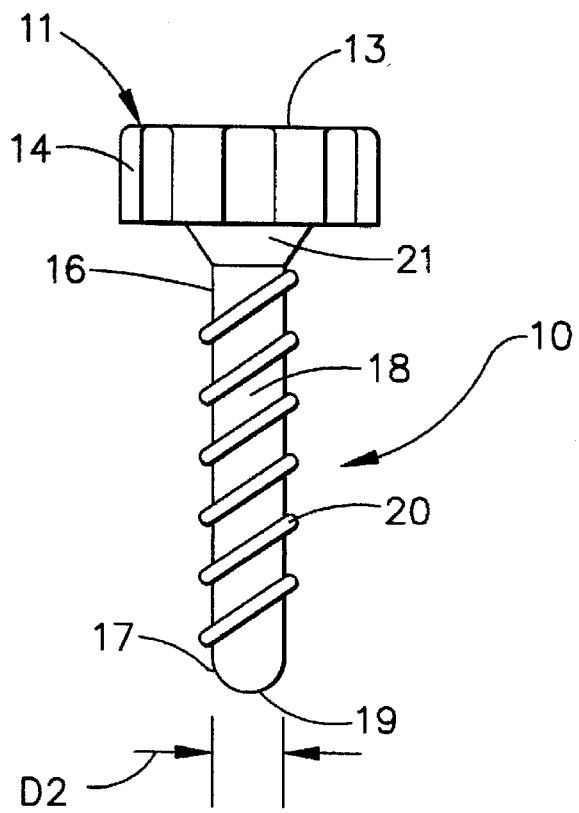
FIGS. 2 and 2a represent a side elevation view and a top plan view, respectively, of another surgical plug within the scope of the claimed invention.
Figure 2A:
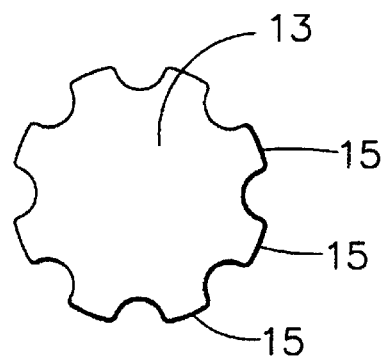

FIGS. 2 and 2a depict another surgical plug of this invention. It too has the same essential elements as the plug illustrated in FIG. 1 and 1a, namely, it has a cap and a shaft. Like parts of the plug are designated with the same numbers as those used for the plug depicted in FIGS. 1 and 1a for convenience. The diameter of the shaft, depicted as "D2" in FIG. 2, is smaller than the shaft diameter of the plug depicted in FIG. 1. The diameter of the shaft can be sized to match a given diameter of an opening in the body wall. However, whatever diameter is chosen for the shaft of the plug, it is preferred that that diameter be slightly greater than the diameter of the opening in the body wall. The cap diameter for each of the plugs shown in FIGS. 1 and 2 is essentially the same. The shaft proximal end of the plug in FIG. 2 has a neck 21 which joins the cylindrical shaft to the underside of the impervious cap.

Figure 3:
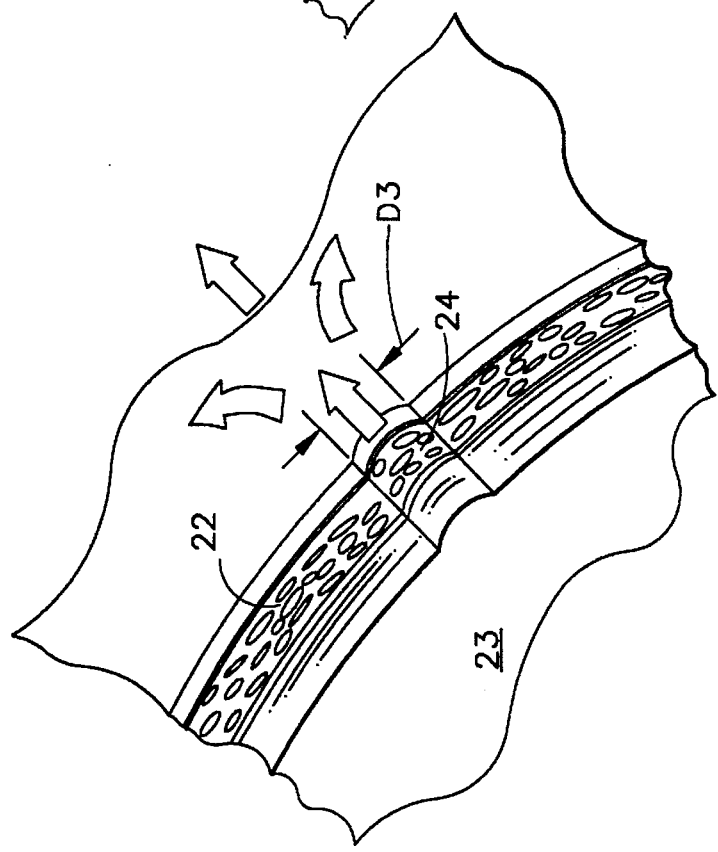

FIG. 3 shows a cross-section of a body wall 22 and an insufflated interior body cavity 23 of a surgical patient. The body wall has an opening 24 through it which provides a passageway from the exterior of the patient to within the interior of the insufflated body cavity. The opening has a diameter which is represented as "D3" in FIG. 3. The opening provides a passageway for the escape of insufflation fluid from the interior body cavity to the exterior of the patient, as illustrated by the arrows emanating from the opening in FIG. 3. Therefore, the surgeon must plug the opening to restrict the escape of insufflation fluid through the passageway created by the opening to maintain the interior body cavity in the insufflated condition.

Figure 4:
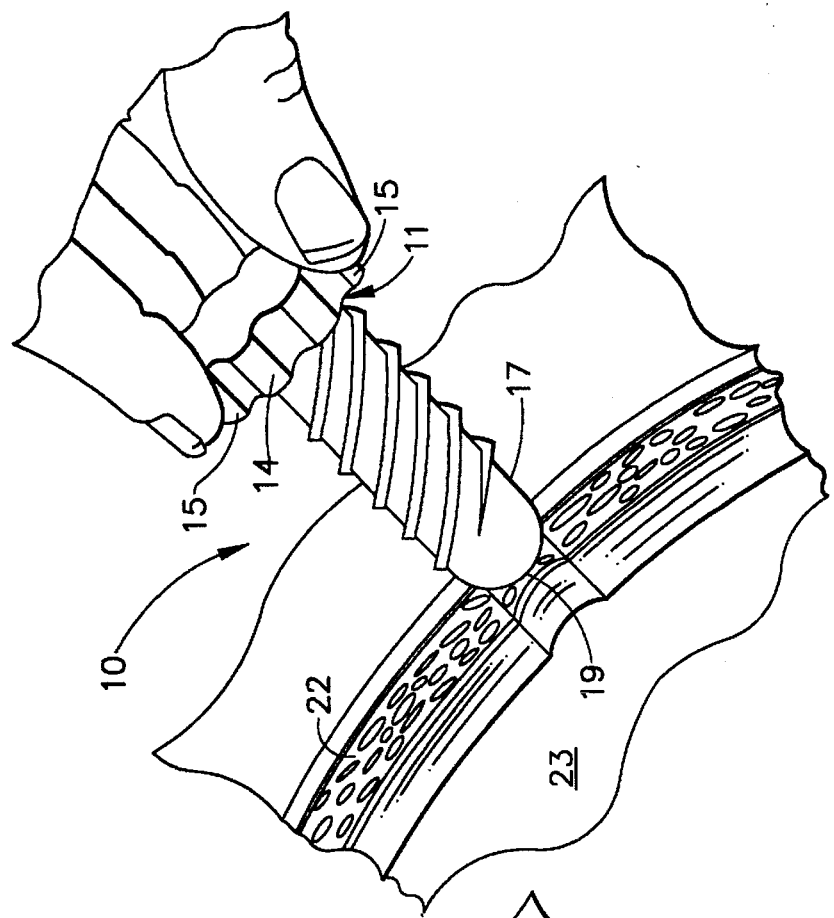
FIGS. 3–6 illustrate a cross-section of an insufflated interior body cavity of a surgical patient, and a method by which the surgical plug depicted in FIG. 1 and 1a, is inserted through an opening in the body wall to minimize leakage of the insufflation fluid during an endoscopic surgical procedure.
Figure 6:
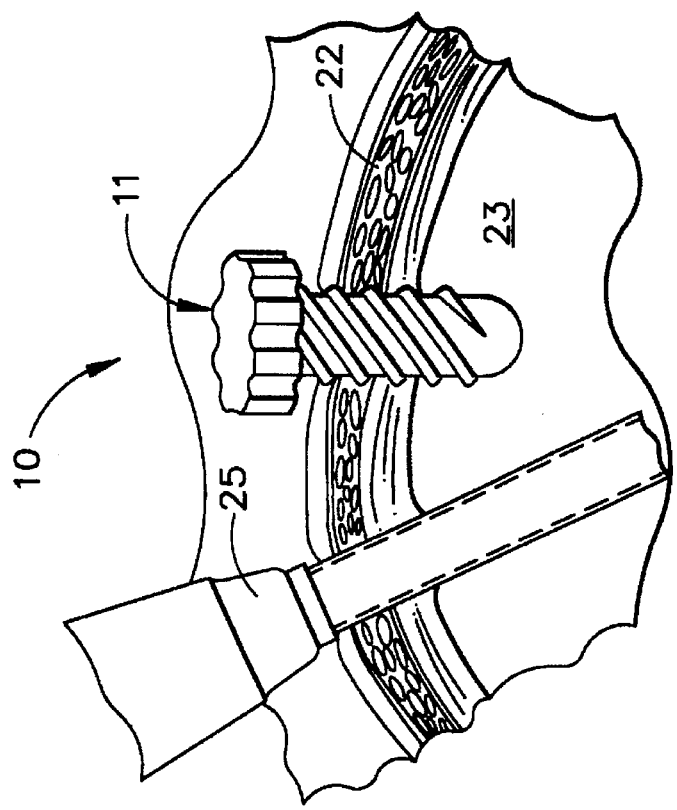
Figure 5:
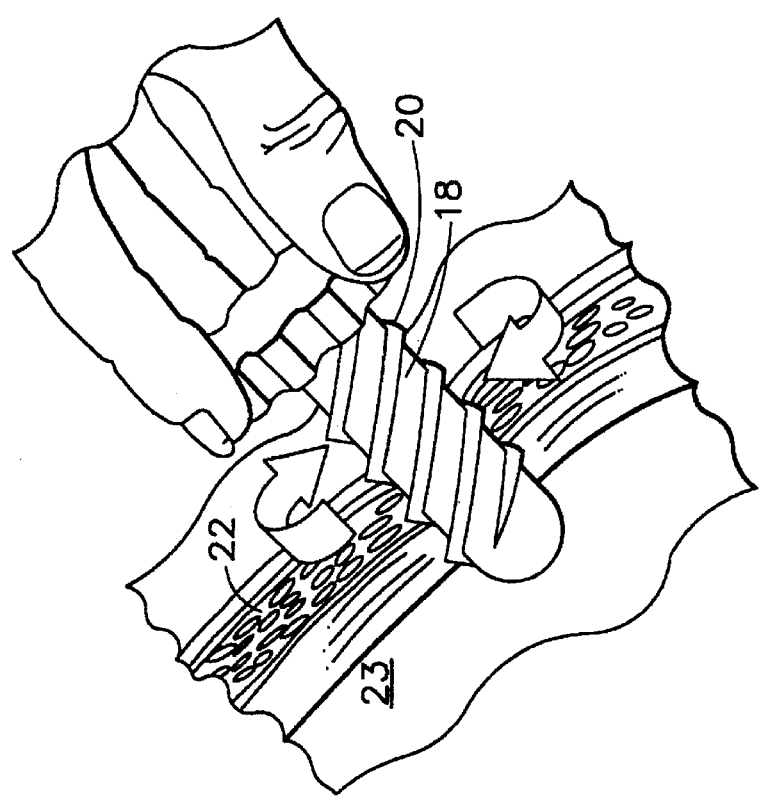

The sequence of steps to insert the ping through the opening into the interior body cavity is illustrated in FIGS. 4–6. The surgeon initially grips the plug 10 by grasping the cap 11 at the knurled ridges 15 of the continuous sidewall surface 14. He positions the blunt tip 19 at the shaft distal end 17 of the plug into the opening. The surgeon then screws the shaft into and through the opening by rotating the shaft in the direction depicted in FIG. 5 using the cap. The helical thread 20 on the outer surface 18 of the shaft enables the surgeon to screw the shaft through the opening. When the shaft is inserted to a point where the cap is adjacent the body wall, the plug has been fully inserted.

The particular sequence of steps shown in FIGS. 4–6 depict the use of the plug illustrated in FIG. 1 and 1a. The diameter of the shaft of this plug, D1, is greater than the diameter of the opening, D3. The larger diameter for the shaft ensures a tight, frictional fit between the shaft and the opening, thus ensuring a secure and tight seal. When the plug is fully inserted the cap is situated external to the body cavity adjacent the body adjacent the body wall, and the shaft extends through the opening into the interior of the body cavity. Since the opening is now adequately sealed, insufflation within the interior hotly cavity can be maintained. This allows the surgeon to carry out other endoscopic surgical procedures with another required surgical instrument 25 (FIG. 6).

Although this invention has been described in connection with the most preferred embodiments, numerous additional embodiments are contemplated. The preferred embodiments are not intended to limit the spirit and scope of the claimed invention, but merely to provide the reader with an understanding of the particular preferred embodiments. The only limitations on the scope of the claimed invention arc set forth in the claims which appear below.

What is claimed is:

1. A one-piece surgical plug for minimizing leakage of insufflation fluid during an endoscopic surgical procedure from within an interior body cavity of a surgical patient through an opening of a given diameter made in a body wall of said patient to provide access to said body cavity, said one-piece plug comprising:

an impervious cap having a diameter greater than said opening diameter, said cap disposable externally of said body cavity and adjacent said body wall for plugging said opening; and a generally solid cylindrical shaft extending from said cap, said solid shaft extendable interiorly into said interior body cavity of said patient, said solid shaft having an outer surface with an outer surface diameter and proximal and distal ends, said outer surface diameter sized so as to provide a friction fit between said shaft and said opening when said shaft is inserted through said opening, and said outer surface having a helical tissue engaging thread thereon from adjacent said proximal end to adjacent said distal end, said thread for facilitating the insertion of said solid shaft through said opening into said interior body cavity.

2. The surgical plug of claim 1 wherein said shaft extends integrally from said cap, and said shaft distal end has a point.

3. The surgical plug of claim 2 wherein said point has a blunt tip.

4. The surgical plug of claim 3 wherein said cap has a substantially flat top surface.

5. The surgical plug of claim 4 wherein said top surface is generally circular, and said cap further comprises a substantially continuous side surface extending integrally from said top surface.

6. The surgical plug of claim 5 wherein said side surface has a plurality of knurled ridges displayed thereon so as to provide a gripping surface.

7. A surgical method of plugging a puncture opening of a given diameter in a body wall of a patient to minimize leakage from an inflated internal body cavity through said opening during an endoscopic surgical procedure, said method comprising the steps of:

a) providing a one-piece surgical plug having an impervious cap with a cap diameter greater than said opening diameter and a generally solid cylindrical shaft extending from said cap, wherein said solid shaft has
      i) a shaft diameter sized so as to provide a frictional fit against said opening diameter,
      ii) an outer surface and proximal and distal ends,
      iii) a helical tissue engaging thread on said outer surface and extending from adjacent said shaft proximal end to adjacent said shaft distal end, and
      iv) a point at said shaft distal end;

b) interesting said point on said shaft distal end of said plug into and through said opening; and c) screwing said solid shaft through said opening until said distal end of said solid shaft descends interiorly into said body cavity and said cap is adjacent to said opening so as to provide a friction fit between said shaft and said puncture opening for ensuring the minimization of leakage from the inflated internal body cavity.

8. The surgical method of claim 7 wherein said point on said shaft distal end has a blunt tip.

9. The surgical method of claim 8 wherein said cap diameter is greater than said shaft diameter.

10. The surgical method of claim 9 wherein said cap has a substantially flat top surface.

11. The surgical method of claim 10 wherein said top surface is generally circular, and said cap further comprises a substantially continuous side surface extending integrally from said top surface.

12. The surgical method of claim 11 wherein said side surface has a plurality of knurled ridges displayed thereon so as to provide a gripping surface.

* * * * *